(12) United States Patent
Matsuzawa et al.

(10) Patent No.: US 8,729,307 B2
(45) Date of Patent: May 20, 2014

(54) PHOTORESPONSIVE IONIC ORGANIC COMPOUND, METHOD OF PRODUCING THE SAME, AND PHOTORESPONSIVE CARBON NANOTUBE DISPERSANT COMPRISING SAID IONIC ORGANIC COMPOUND

(75) Inventors: Yoko Matsuzawa, Tsukuba (JP); Masaru Yoshida, Tsukuba (JP); Harumi Ohyama, Tsukuba (JP); Haruhisa Kato, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 71 days.

(21) Appl. No.: 13/504,107

(22) PCT Filed: Oct. 26, 2010

(86) PCT No.: PCT/JP2010/068996
§ 371 (c)(1),
(2), (4) Date: Apr. 25, 2012

(87) PCT Pub. No.: WO2011/052604
PCT Pub. Date: May 5, 2011

(65) Prior Publication Data
US 2012/0217151 A1    Aug. 30, 2012

(30) Foreign Application Priority Data
Oct. 26, 2009  (JP) .................. 2009-245064

(51) Int. Cl.
*C07C 211/63*  (2006.01)

(52) U.S. Cl.
CPC .................. *C07C 211/63* (2013.01)
USPC .......................... 564/282; 524/379

(58) Field of Classification Search
CPC .................................... C07C 211/63
USPC .......................... 564/282; 524/379
See application file for complete search history.

(56) References Cited

U.S. PATENT DOCUMENTS

| | | | | |
|---|---|---|---|---|
| 4,509,948 A * | 4/1985 | Wild et al. | ..... | 534/603 |
| 4,656,256 A * | 4/1987 | Colberg et al. | ..... | 534/603 |
| 4,665,162 A * | 5/1987 | Doswald et al. | ..... | 534/589 |
| 5,879,413 A * | 3/1999 | Pengilly et al. | ..... | 534/603 |
| 8,519,040 B2 * | 8/2013 | Yoshida et al. | ..... | 524/379 |
| 2008/0210907 A1 | 9/2008 | Yoshida et al. | | |
| 2010/0126386 A1 * | 5/2010 | Haremza et al. | ..... | 252/182.12 |

FOREIGN PATENT DOCUMENTS

| | | |
|---|---|---|
| JM | 2004-2850 A | 1/2004 |
| JP | 2000-212132 A | 8/2000 |
| JP | 2000-229917 A | 8/2000 |
| JP | 2004-353017 A | 12/2004 |
| JP | 2005-126740 A | 5/2005 |
| JP | 2007-153716 A | 6/2007 |
| JP | 2009-23886 A | 2/2009 |
| WO | WO 2006/082768 A1 | 8/2006 |
| WO | WO 2010/027067 A1 | 3/2010 |
| WO | WO 2011/052601 A1 | 5/2011 |

OTHER PUBLICATIONS

D. T. Chen et al.: "Photoisomerization and Fluorescence of Chromophores Built into the Backbones of Flexible Polymer Chains", Macromolecules, 1976, vol. 9, pp. 463-468.
I. Willner et al.: "Reversible Light-Stimulated Activation and Deactivation of alpha-Chymotrypsin by Its Immobilization in Photoisomerizable Copolymers", J. Am. Chem. Soc., 1993, vol. 115, pp. 8690-8694.
J. Chen et al.: "Solution Properties of Single-Walled Carbon Nanotubes", Science, vol. 282, 1998, pp. 95-98.
K. Nobusawa et al.: "Reversible Solubilization and Precipitation of Carbon Nanotubes through Oxidation-Reduction Reactions of a Solubilizing Agent", Angew. Chem. Int. Ed., 2008, 47, pp. 4577-4580.
M. Irie et al.: "Photoresponsive Polymers. 2. 1 Reversible Solution Viscosity Change of Polyamides Having Azobenzene Residues in the Main Chain", Macromolecules, 1981, vol. 14, pp. 262-267.
M. Irie et al.: "Photoresponsive Polymers. On the Dynamics of Conformational Changes of Polyamides with Backbone Azobenzene Groups", Macromolecules, 1981, vol. 14, pp. 1246-1249.
PCT/ISA/210—International Search Report dated Dec. 7, 2010, issued in PCT/JP2010/068996.
S. Chen et al.: "Light-Controlled Single-Walled Carbon Nanotube Dispersions in Aqueous Solution", Langmuir, 2008, vol. 24, pp. 9233-9236.
S. Iijima et al.: "Single-Shell carbon nanotube of 1-nm diameter", Nature, vol. 363, Jun. 17, 1993, pp. 603-605.
S. Iijima: "Helical microtubules of graphite carbon", Nature, vol. 354, Nov. 7, 1991, pp. 56-58.
Y. Majima et al.: "A new displacement current measuring system coupled with the Langmuir film technique", Rev. Sci. Instrum., 1991, vol. 62, pp. 2228-2233.
Y. Majima at al.: "Reversible Displacement Current Generation Due to Photochromism in a Spread Monolayer: Influence of Molecular Orientation", Jpn. J. Appl. Phys. vol. 31, pp. 864-867.

\* cited by examiner

*Primary Examiner* — Robert Havlin
(74) *Attorney, Agent, or Firm* — Birch, Stewart, Kolasch & Birch, LLP

(57) ABSTRACT

A photoresponsive ionic organic compound of formula (I); a method of producing the same; a photoresponsive carbon nanotube (CNT) dispersant; a CNT dispersion containing the dispersant; and a method of separating a CNT from the dispersion:

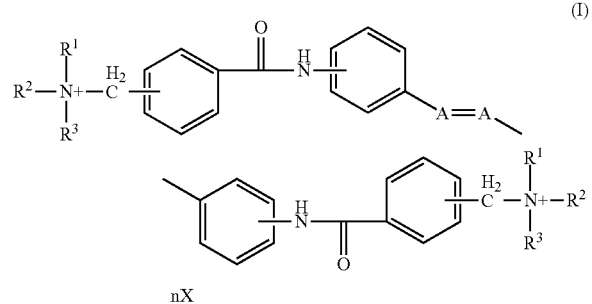

wherein $R^1$, $R^2$, and $R^3$ each represent a hydrogen atom or an alkyl group; A represents —CH— or a nitrogen atom; X represents an anion; and n is a number to give a charge of –2 to nX.

11 Claims, 9 Drawing Sheets

US 8,729,307 B2

PHOTORESPONSIVE IONIC ORGANIC COMPOUND, METHOD OF PRODUCING THE SAME, AND PHOTORESPONSIVE CARBON NANOTUBE DISPERSANT COMPRISING SAID IONIC ORGANIC COMPOUND

TECHNICAL FIELD

The present invention relates to a photoresponsive ionic organic compound that is useful as a carbon nanotube dispersant and has a photochromic functional group in the molecule, and to a method of producing the same. Further, the present invention relates to a carbon nanotube dispersion using the compound as a dispersant, and to a method of separating a carbon nanotube from the dispersion, by irradiating the dispersion with light, to control the dispersibility of the carbon nanotube.

BACKGROUND ART

Carbon nanotubes (CNTs) have been attracting attentions in recent years as new materials for nanotechnologies (Non-patent Literature 1). Among these, single-walled carbon nanotubes (SWCNTs) are expected to be applied to various fields, owing to their simple structures and specific physical and chemical properties.

However, due to the association (bundling) by the strong van der Waals interaction of the CNTs themselves, it is quite difficult to solubilize or disperse CNTs in solvents, which is a conspicuous hindrance for the development and application of materials.

Hitherto, various studies have been made chemically or physically with respect to methods of solubilizing CNTs in solvents. Proposals include a technique for forming a functional group that enhance the solubility of a CNT in a solvent by ultrasonification of the CNT in an acidic solution (Non-patent Literature 2), and a technique for accelerating dispersion (solubilization) in a solvent by mixing with a dispersant. The dispersants reported include ionic amphipathic compounds, compounds having an aromatic functional group, naturally-occurring polymers, synthetic polymers, and the like (Patent Literature 1). However, in many cases of them, there is no alternative but to remove the dispersant that has been adsorbed on the CNT by washing for a long time period, calcination, or removing by decomposition by an agent. Thus, it is still required to develop a dispersant that can be readily removed for taking out a pure CNT. Furthermore, it is also important in view of resource saving, to develop a dispersant having recyclability that can be utilized repeatedly, by repeatedly controlling the dispersibility as necessary, and causing reaggregation of the dispersed CNT to collect the same appropriately.

Until now, several examples are known, in which the dispersibility was controlled, by changing the structure and solubility of a dispersant by any conditions. For example, in Non-patent Literature 3, a CNT is dispersed in the form of a micelle, by using an amphipathic compound, which is malachite green, as a dye, substituted to have polyethylene glycol, and the thus-dispersed CNT is caused reaggregation, by utilizing the change in solubility by photodecomposition ionization of the malachite green by light irradiation. Furthermore, in Patent Literature 2, a CNT is dispersed, by using an amphipathic oligopeptide as a dispersant, and then only the dispersant is decomposed biochemically by using a protease, to isolate the CNT precipitated. On the other hand, in Non-patent Literature 4 and Patent Literature 3, a dispersant composed of a metal complex is synthesized, and using this, the dispersibility is suitably changed by controlling the affinity to a CNT, by utilizing the change in conformation (=the change in molecular structure) by chemical oxidation/reduction of the central metal.

However, problems to be solved still remain in either case of above. For example, the dispersant derived from malachite green in Non-patent Literature 3 requires an addition amount of ten times greater than that of the CNT on the basis of weight ratio, and thus it cannot be considered that the CNT is dispersed efficiently. Furthermore, in the method of collecting a pure CNT by the biochemical decomposition of the dispersant in Patent Literature 2, it is difficult to collect and reuse the dispersant, since the utilization is limited to only under a condition in which the enzyme exhibits the activity due to its principle, and the decomposition is irreversible. In Non-patent Literature 4 and Patent Literature 3, although dispersion and aggregation can be controlled reversibly, a high-output ultrasonic irradiation method and a high-speed vibration milling method that requires special apparatus are used in combination so as to solubilize the CNT, and thus the manner for preparing the dispersion cannot be considered to be convenient. Furthermore, since chloroform, an amide-based organic solvent, or the like is used as a dispersion medium, environmental load is concerned when a condition in which the dispersion medium is used industrially in a large amount is taken into consideration.

Patent Literature 1: JP-A-2004-2850 ("JP-A" means unexamined published Japanese patent application) (published date: Jan. 8, 2004)
Patent Literature 2: JP-A-2007-153716 (published date: Jun. 21, 2007)
Patent Literature 3: JP-A-2009-23886 (published date: Feb. 5, 2009)
Non-Patent Literature 1: S. Iijima, Nature, 354, 56 (1991), S. Iijima, T. Ichihashi, Nature, 363, 603 (1993)
Non-Patent Literature 2: J. Chen, et al, Science, 282, 95 (1998)
Non-Patent Literature 3: S. Chen, et al., Langmuir, 24, 9233 (2008)
Non-Patent Literature 4: K. Nobusawa et al., Angew. Chem. Int. Ed., 47, 4577 (2008)

DISCLOSURE OF INVENTION

Technical Problem

As mentioned above, although various studies have been done on methods of producing a CNT dispersion, it cannot be considered that the development is sufficient on a dispersant that can control dispersing of a CNT conveniently, effectively and repeatedly and that can accelerate solubilization in water that does not put any load on the environment.

The present invention has been made in view of the above-mentioned problem, and an object of the present invention is to provide a technique by which a CNT is dispersed stably in a solvent (water) that does not put any load on the environment, the dispersed state thereof can be controlled conveniently, efficiently and effectively, and the dispersed state can be changed repeatedly, and further to provide a technique that achieves this by highly-directed stimulation, i.e. light.

Solution to Problem

In view of the above-mentioned problem, the inventors of the present invention, having intensively studied, newly synthesized an ionic organic compound having a photochromic moiety, to find uniquely that a CNT can be dispersed conveniently and effectively in an aqueous solution, by using the compound as a dispersant, and that the dispersibility of the CNT can be controlled, by a photoisomerization reaction of the dispersant by light irradiation. Thus, the inventors attained to complete the present invention, based on this finding.

That is, according to the present invention, there is provided the following inventions:

(1) A photoresponsive ionic organic compound, represented by formula (I):

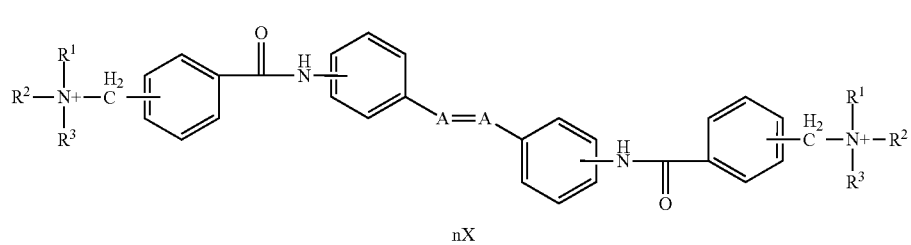

wherein $R^1$, $R^2$, and $R^3$ each represent a hydrogen atom or an alkyl group; A represents a carbon atom or a nitrogen atom; X represents an anion; and n is a number to give a charge of −2 to nX.

(2) The photoresponsive ionic organic compound according to (1), wherein, in formula (I), X is at least one selected from a halogen atom (F, Cl, Br, I), a tetrafluoroborate group ($BF_4$), hexafluorophosphate ($PF_6$), bis(trifluoromethanesulfonyl)imido, thioisocyanate (SCN), a nitrate group ($NO_3$), a sulfate group ($SO_4$), a thiosulfate group ($S_2O_3$), a carbonate group ($CO_3$), a hydrogencarbonate group ($HCO_3$), a phosphate group, a phosphite group, a phosphinate group, a halogen acid compound acid group ($AO_4$, $AO_3$, $AO_2$, AO: A=Cl, Br, I), a tris(trifluoromethylsulfonyl)carbonate group, a trifluoromethylsulfonate group, a dicyanamido group, an acetate group ($CH_3COO$), a halogenated acetate group (($CA_nH_{3-n}$)COO; A=F, Cl, Br, I; n=1, 2, 3), and a tetraphenylborate group ($BPh_4$) and a derivative thereof ($B(Aryl)_4$: Aryl=a substituted phenyl group).

(3) A method of producing the ionic organic compound according to (1), which method comprises: subjecting (A) a photoresponsive aromatic diamide compound having a (chloromethyl)benzamido group on the respective end, represented by formula (II), and (B) an amine represented by formula (III), to a quaternization reaction:

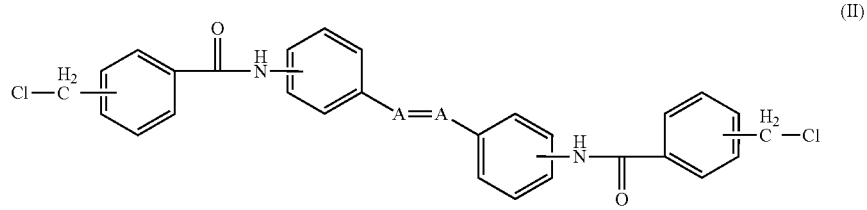

wherein A represents a carbon atom or a nitrogen atom; and

wherein $R^1$, $R^2$, and $R^3$ each represent a hydrogen atom or an alkyl group.

(4) The method of producing the ionic organic compound according to (3), wherein the quaternization reaction is conducted in dimethylformamide at from 50 to 80° C.

(5) The method of producing the photoresponsive ionic organic compound according to (3) or (4), which method further comprises: substituting the anion of the thus-obtained photoresponsive ionic compound with another anion by an anion exchange reaction.

(6) A photoresponsive CNT dispersant, comprising the photoresponsive ionic organic compound according to (1).

(7) The photoresponsive CNT dispersant according to (6), which has a self-diffusion coefficient that changes in response to light.

(8) A CNT dispersion, containing the photoresponsive CNT dispersant according to (6) or (7).

(9) A method of separating a CNT from the dispersion, which method comprises: controlling a dispersibility of the CNT with the photoresponsive CNT dispersant according to (6) or (7), by irradiating the CNT dispersion according to (8) with light of a suitable wavelength, to change a molecular structure of the dispersant, thereby to change an affinity thereof with the CNT.

Advantageous Effects of Invention

By using the dispersant of the present invention, an aqueous solution can be provided, in which a CNT is dispersed conveniently and effectively. The dispersion is useful for the development of novel composite materials containing a CNT as an elemental raw material (CNT-containing membranes, CNT-containing paints, and the like). Furthermore, the present invention can control the dispersibility of the CNT, by reversibly changing the chemical structure of the dispersant by light irradiation. Since a wavelength, intensity, polarized light, and the like, of light can be suitably selected, it becomes possible to conduct precise control, according to the situation. Thus, the dispersant of the present invention can be readily separated from the CNT, in the dispersion process for the CNT, such as the separation and purification of the CNT immediately after the production, and can be utilized repeatedly.

BEST MODE FOR CARRYING OUT THE INVENTION

Figure 1:
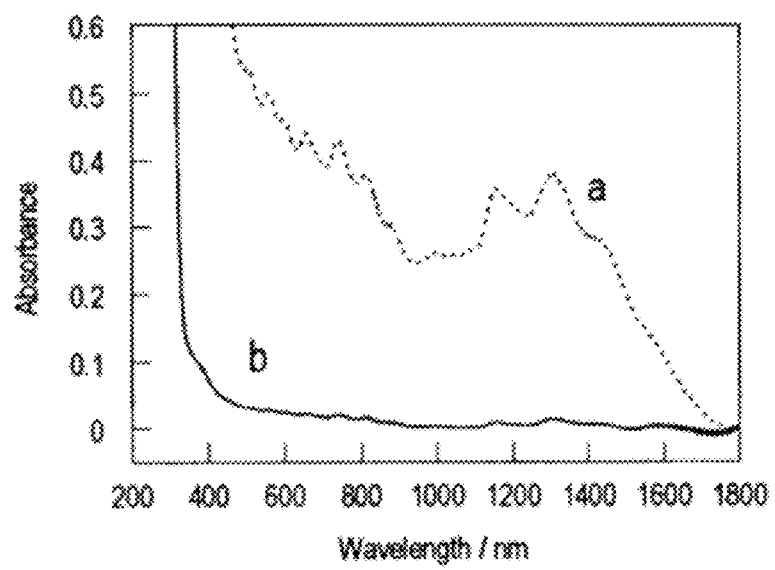
FIG. 1 is a graph showing the Vis-NIR spectrum of the SWCNT dispersion when the ionic organic compound (12) was used in Example 12.

Next, the best mode for carrying out the present invention will be explained by way of the examples, but the present invention is not construed to be limited by these examples. All modifications and other embodiments or examples within the technical concept of the present invention are encompassed in the present invention.

EXAMPLES

Hereinafter, the present invention will be described concretely with reference to the examples, but the present invention is not limited to those specified examples.

In the following examples, 4-(chloromethyl)benzoylchloride, 4,4-diaminostilbene dihydrochloride, ethyldimethylamine, n-butyldimethylamine, and 3-nitroaniline that are raw materials for the production of photoresponsive organic ion compounds were purchased from Tokyo Chemical Industry Co., Ltd. and used. n-Hexyldimethylamine, 4,4'-diaminoazobenzene, dehydrated methylene chloride, N,N-dimethylformamide, ethyl acetate, and n-hexane were purchased from Kanto Kagaku and used. Triethylamine and ethylenediamine were purchased from Wako Pure Chemical Industries, Ltd. and used. Lithium bis(trifluoromethanesulfonyl)imide was purchased from Kishida Chemical Co., Ltd. and used.

Example 1 m-Nitroaniline (6 g, 0.04 mol) and ethylenediamine (15 g, 0.3 mol) were placed in a pressure-resistant sealing flask, followed by heating at 150° C. for 22 hours. The thus-obtained reaction product was dispersed in water, followed by separating the resultant precipitate by filtration, to give a crude product. The crude product was purified by silica gel column chromatography (ethyl acetate:hexane=5:1), to give the target compound represented by formula (2) as a yellow powder. Yield was 0.69 g, 10%. The structure of the thus-obtained compound was identified by the $^1$H NMR spectrum of the compound.

$^1$H-NMR (300 MHz, DMSO-d$_6$, δ) 5.39 (s, 4H), 6.71 to 6.74 (m, 2H), 7.01 to 4.07 (m, 4H), 7.18 to 7.23 (m, 2H)

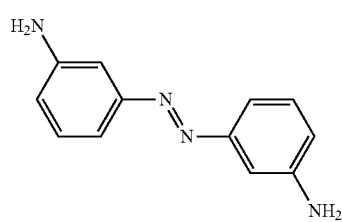

(2)

The compound represented by formula (2) (0.64 g, 3.0 mmol) and triethylamine (0.67 g, 6.6 mmol) were dissolved in dehydrated methylene chloride (50 mL). Thereto, a solution of 4-chloromethylbenzoyl chloride (1.13 g, 6.0 mmol) in dehydrated methylene chloride (50 mL) was added under stirring over 1 hour, followed by stirring at room temperature for 16 hours. The resultant precipitate was separated by filtration, to give the target compound represented by formula (3) as a yellow powder. Yield was 1.35 g, 86%. The structure of the thus-obtained compound was identified by the $^1$H and $^{13}$C NMR spectra of the compound.

$^1$H-NMR (300 MHz, DMSO-d$_6$, δ) 4.86 (s, 4H), 7.61 to 7.71 (m, 8H), 7.97 to 8.03 (m, 6H), 8.43 (s, 2H), 10.55 (s, 2H)
$^{13}$C-NMR (75 MHz, DMSO-d$_6$, δ) 45.31, 113.04, 119.04, 123.04, 128.11, 128.74, 129.61, 134.40, 140.12, 141.17, 152.12, 165.28

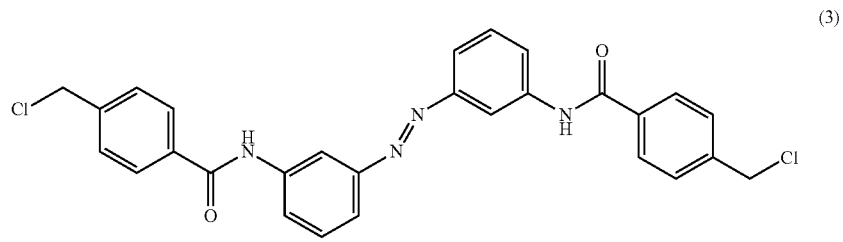 [SMILES: O=C(Nc1cccc(/N=N/c2cccc(NC(=O)c3ccc(CCl)cc3)c2)c1)c1ccc(CCl)cc1]

(3)

The compound represented by formula (3) (0.36 g, 0.7 mmol) and n-butyldimethylamine (0.21 g, 2.1 mmol) were stirred under heating in dimethylformamide (40 mL) at 80° C. for 48 hours. After cooling to room temperature, the resultant precipitate was separated by filtration, to give the ionic organic compound represented by formula (4) at a yield of 62%. The structure of the thus-obtained compound was identified by the $^1$H and $^{13}$C NMR spectra of the compound.

$^1$H-NMR (300 MHz, DMSO-d$_6$, δ) 0.97 (t, J=7.1 Hz, 6H), 1.34 (qt, J=7.1 Hz, 4H), 1.80 (br, 4H), 3.00 (s, 12H), 3.27 (br, 4H), 4.64 (s, 4H), 7.62 (t, J=7.9 Hz, 2H), 8.17 (d, J=8.2 Hz, 4H), 8.48 (s, 2H), 10.74 (s, 2H)

$^{13}$C-NMR (75 MHz, DMSO-d$_6$, δ) 13.45, 19.19, 23.71, 49.19, 63.45, 65.36, 113.32, 119.04, 123.25, 128.18, 129.59, 131.49, 132.94, 135.89, 140.05, 152.10, 164.99

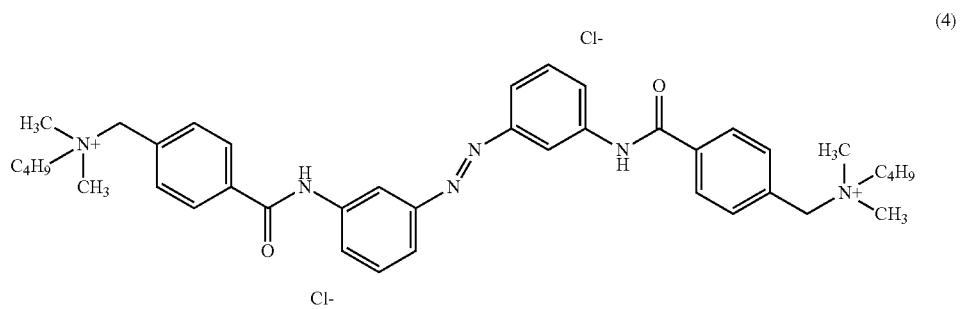

(4)

Example 2

The ionic organic compound represented by formula (5) was obtained in the same manner as in Example 1, except that n-ethyldimethylamine was used in place of n-butyldimethylamine in Example 1. Yield was 85%. The structure of the thus-obtained compound was identified by the $^1$H and $^{13}$C NMR spectra of the compound.

$^1$H-NMR (300 MHz, DMSO-d$_6$, δ) 1.37 (t, J=7.0 Hz, 6H), 2.98 (s, 12H), 3.38 to 3.40 (m, 4H), 4.62 (s, 4H), 7.60 to 7.65 (m, 2H), 7.70 to 7.76 (m, 6H), 8.01 (d, J=8.0 Hz, 2H), 8.17 (d, J=8.2 Hz, 4H), 8.48 (s, 2H), 10.73 (s, 2H)

$^{13}$C-NMR (75 MHz, DMSO-d$_6$, δ) 7.91, 48.22, 60.84, 62.30, 113.28, 119.11, 122.51, 128.15, 129.60, 131.48, 132.95, 135.86, 140.04, 152.11, 165.00

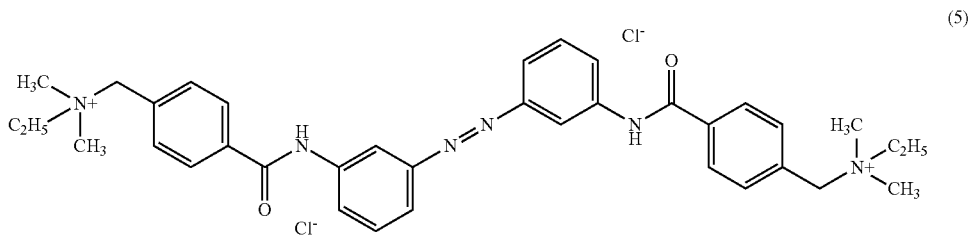 [SMILES: [Cl-] ; CC[N+](C)(C)Cc1ccc(C(=O)Nc2cccc(N=Nc3cccc(NC(=O)c4ccc(C[N+](C)(C)CC)cc4)c3)c2)cc1 ; [Cl-]]

(5)

Example 3

The target compound represented by formula (6) was obtained in the same manner as in Example 1, except that 4,4'-diaminoazobenzene was used in place of the compound represented by formula (2) in Example 1. Yield was 4.65 g, 89%. The structure of the thus-obtained compound was identified by the $^1$H and $^{13}$C NMR spectra of the compound.

$^1$H-NMR (300 MHz, DMSO-d$_6$, δ) 4.86 (s, 4H), 7.62 (d, J=8.4 Hz, 4H), 7.92 (d, J=8.9 Hz, 4H), 7.99 to 8.05 (m, 8H), 10.60 (s, 2H)

$^{13}$C-NMR (75 MHz, DMSO-d$_6$, δ) 45.31, 120.40, 123.16, 128.12, 128.74, 134.41, 14123, 141.82, 147.87, 165.35

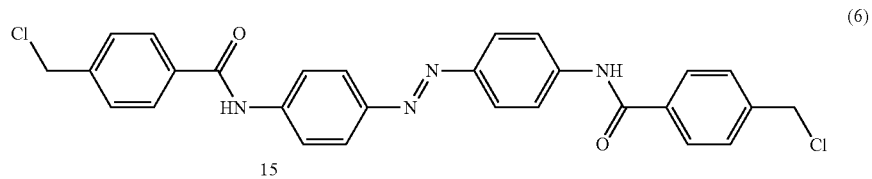

(6)

The ionic organic compound represented by formula (7) was obtained in the same manner as in Example 1, except that the compound represented by formula (6) was used in place of the compound represented by formula (3) and that n-hexyldimethylamine was used in place of n-butyldimethylamine in Example 1. Yield was 83%. The structure of the thus-obtained compound was identified by the $^1$H and $^{13}$C NMR spectra of the compound.

$^1$H-NMR (300 MHz, DMSO-d$_6$, δ) 0.88 to 0.92 (m, 6H), 1.32 (br, 12H), 1.81 (br, 4H), 3.00 (s, 12H), 3.27 to 3.31 (m, 4H), 4.64 (s, 4H), 7.74 (d, J=8.2 Hz, 4H), 7.93 (d, J=8.9 Hz, 4H), 8.08 (d, J=9.0 Hz, 4H), 8.15 (d, =8.2 Hz, 4H), 10.80 (s, 2H)

$^{13}$C-NMR (75 MHz, DMSO-d$_6$, δ) 13.75, 21.69, 21.78, 25.41, 30.61, 49.18, 63.69, 65.38, 120.58, 123.15, 128.22, 131.53, 132.94, 135.92, 141.75, 147.95, 165.07

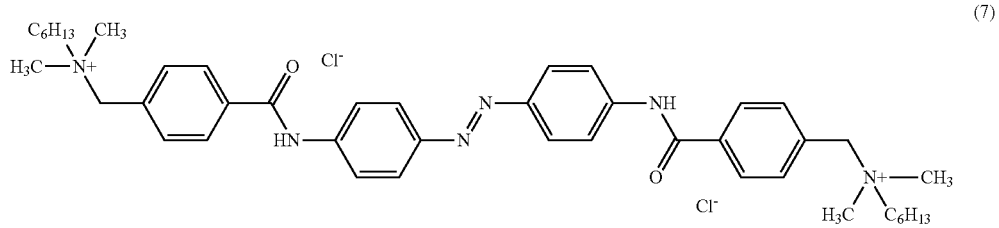

(7)

Example 4

The ionic organic compound represented by formula (8) was obtained in the same manner as in Example 1, except that the compound represented by formula (6) was used in place of the compound represented by formula (3) in Example 1. Yield was 79%. The structure of the thus-obtained compound was identified by the $^1$H and $^{13}$C NMR spectra of the compound.

$^1$H-NMR (300 MHz, DMSO-d$_6$, δ) 0.97 (t, J=7.2 Hz, 6H), 1.34 (qt, J=7.7 Hz, 4H), 1.80 (br, 4H), 3.00 (s, 12H), 3.29 (br, 4H), 4.64 (s, 4H), 7.74 (d, =8.9 Hz, 4H), 8.08 (d, J=8.9 Hz, 4H), 8.15 (d, =8.1 Hz, 4H), 10.79 (s, 2H)

$^{13}$C-NMR (75 MHz, DMSO-d$_6$, δ) 13.45, 19.19, 23.71, 49.19, 63.46, 65.34, 120.59, 123.13, 128.24, 131.53, 132.94, 135.91, 141.76, 147.94, 165.06

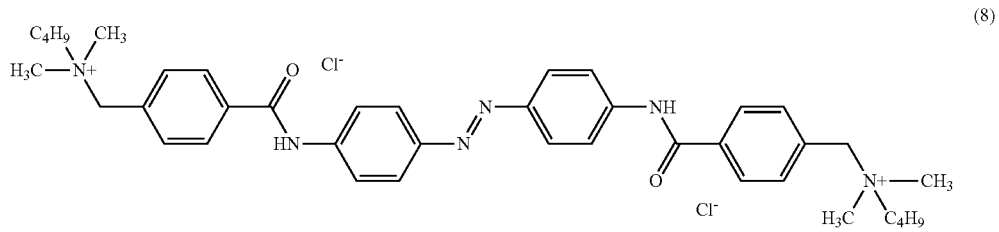

(8)

Example 5

The target compound represented by formula (9) was obtained in the same manner as in Example 1, except that 4,4-diaminostilbene dihydrochloride was used in place of the compound represented by formula (2) in Example 1. Yield was 1.83 g, 98%. The resultant product was a compound which is sparingly soluble in a solvent.

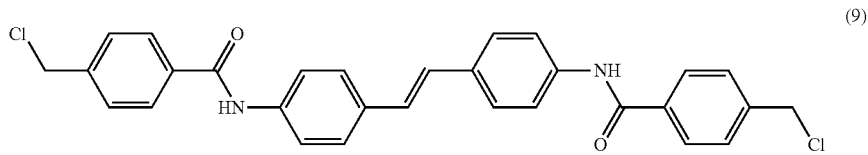 [SMILES: O=C(Nc1ccc(/N=N/c2ccc(NC(=O)c3ccc(CCl)cc3)cc2)cc1)c1ccc(CCl)cc1]

(9)

The ionic organic compound represented by formula (10) was obtained in the same manner as in Example 1, except that the compound represented by formula (9) was used in place of the compound represented by formula (3) and that ethyldimethylamine was used in place of n-butyldimethylamine in Example 1. Yield was 98%. The structure of the thus-obtained compound was identified by the $^1$H and $^{13}$C NMR spectra of the compound.

$^1$H-NMR (300 MHz, DMSO-d$_6$, δ) 1.36 (t, J=7.1 Hz, 6H), 2.97 (s, 12H), 3.37 to 3.42 (m, 4H), 4.61 (s, 4H), 7.19 (s, 2H), 7.60 (d, J=8.7 Hz, 4H), 7.73 (d, J=8.3 Hz, 4H), 7.85 (d, J=8.6 Hz, 4H), 8.12 (d, J=8.2 Hz, 4H), 10.52 (s, 2H)

$^{13}$C-NMR (75 MHz, DMSO-d$_6$, δ) 7.00, 47.67, 58.25, 64.08, 119.62, 125.63, 125.95, 127.19, 130.40, 131.85, 132.00, 135.21, 137.40, 163.73

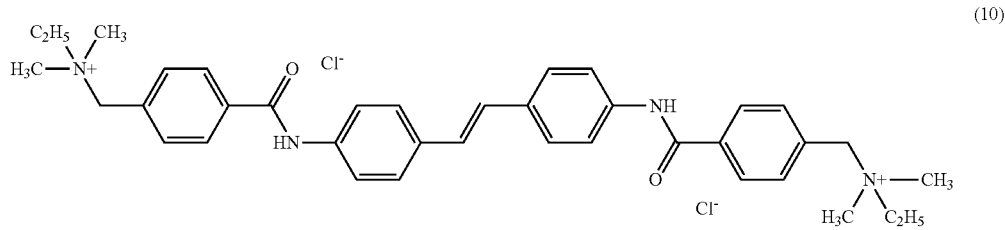

(10)

Example 6

The ionic organic compound represented by formula (11) was obtained in the same manner as in Example 1, except that the compound represented by formula (9) was used in place of the compound represented by formula (3) and that n-hexyldimethylamine was used in place of n-butyldimethylamine in Example 1. Yield was 73%. The structure of the thus-obtained compound was identified by the $^1$H and $^{13}$C NMR spectra of the compound.

$^1$H-NMR (300 MHz, DMSO-d$_6$, δ) 0.87 to 0.92 (m, 6H), 1.32 (br, 12H), 1.81 (br, 4H), 2.99 (s, 12H), 3.26 to 3.32 (m, 4H), 4.62 (s, 4H), 7.19 (s, 2H), 7.60 (d, J=8.6 Hz, 4H), 7.72 (d, J=8.1 Hz, 4H), 7.84 (d, J=8.6 Hz, 4H), 8.12 (d, J=8.1 Hz, 4H), 10.52 (s, 2H)

$^{13}$C-NMR (75 MHz, DMSO-d$_6$, δ) 13.75, 21.69, 21.78, 25.41, 30.61, 49.17, 63.68, 65.41, 120.47, 126.55, 126.85, 128.08, 131.28, 132.76, 132.89, 136.17, 138.27, 1364.61

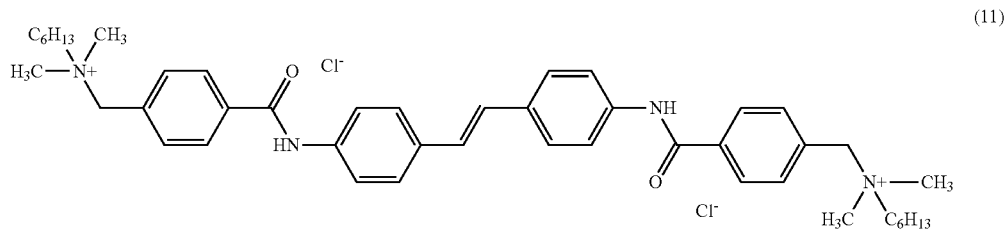

(11)

Example 7

The ionic organic compound represented by formula (12) was obtained in the same manner as in Example 1, except that the compound represented by formula (9) was used in place of the compound represented by formula (3) in Example 1. Yield was 73%. The structure of the thus-obtained compound was identified by the $^1$H and $^{13}$C NMR spectra of the compound.

$^1$H-NMR (300 MHz, DMSO-$d_6$, δ) 0.97 (t, J=7.2 Hz, 6H), 1.34 (qt, J=7.3 Hz, 4H), 1.78 to 1.83 (m, 4H), 3.00 (s, 12H), 3.27 (br, 4H), 4.63 (s, 4H), 7.19 (s, 2H), 7.60 (d, J=8.8 Hz, 4H), 7.72 (d, J=8.3 Hz, 4H), 7.85 (d, J=8.7 Hz, 4H), 8.12 (d, J=8.3 Hz, 4H), 10.51 (s, 2H)

$^{13}$C-NMR (75 MHz, DMSO-$d_6$, δ) 13.45, 19.19, 23.71, 49.17, 63.44, 65.37, 120.47, 126.53, 126.85, 128.08, 131.27, 132.75, 132.89, 136.15, 138.28, 164.60

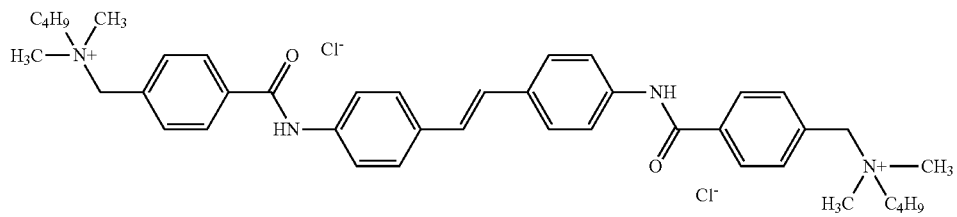

(12)

Example 8

Anion Exchange Reaction

The ionic compound represented by formula (4) (100 mg) obtained in Example 1 was dissolved in water (14 mL) at 100° C. To the resultant solution, a 0.4-M aqueous solution of lithium bis(trifluoromethanesulfonyl)amide (Li-TFSA) (5.0 mL) was added, to form a precipitate of the compound represented by formula (13). Yield was 84%. The structure of the thus-obtained compound was identified by the $^1$H NMR spectrum of the compound.

$^1$H-NMR (300 MHz, DMSO-$d_6$, δ) 0.97 (t, J=7.2 Hz, 6H), 1.34 (qt, J=7.0 Hz, 4H), 1.81 (br, 4H), 2.99 (s, 12H), 3.26 (br, 4H), 4.60 (s, 4H), 7.63 (t, J=8.0 Hz, 2H), 7.73 (d, J=8.3 Hz, 6H), 7.97 (d, J=8.8 Hz, 2H), 8.14 (d, J=8.3 Hz, 4H), 8.47 (s, 2H), 10.64 (s, 2H)

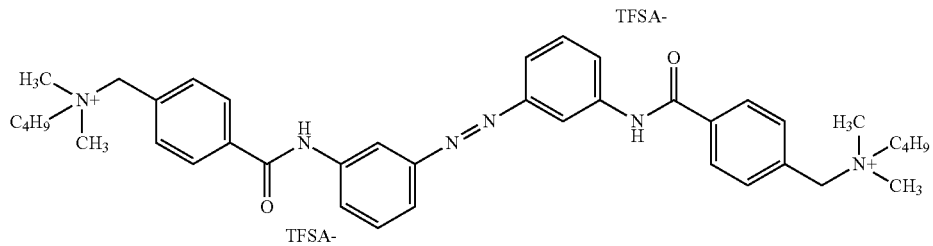

(13)

Example 9

The ionic compound represented by formula (14) was obtained in the same manner as in Example 8, except that the compound of formula (5) was used in place of the ionic compound represented by formula (4) in Example 8. Yield was 100%. The structure of the thus-obtained compound was identified by the $^1$H NMR spectrum of the compound.

$^1$H-NMR (300 MHz, DMSO-$d_6$, δ) 1.37 (t, J=7.2 Hz, 6H), 2.97 (s, 12H), 3.36 to 3.39 (m, 4H), 4.59 (s, 4H), 7.63 (t, J=8.0 Hz, 2H), 7.71 to 7.74 (m, 6H), 7.97 (d, J=8.7 Hz, 2H), 8.13 (d, J=8.3 Hz, 4H), 8.47 (s, 2H), 10.63 (s, 2H)

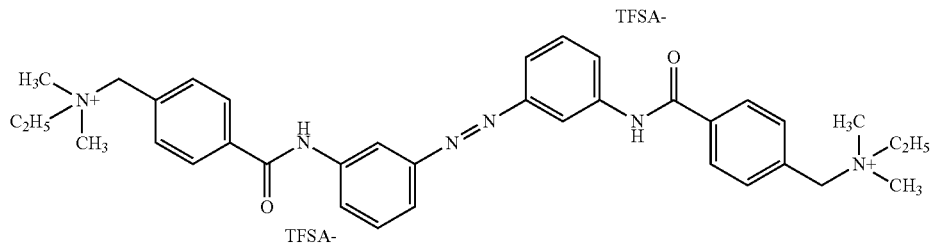

(14)

Example 10

The ionic compound represented by formula (15) was obtained in the same manner as in Example 8, except that the compound of formula (7) was used in place of the ionic compound represented by formula (4) in Example 8. Yield was 78%. The structure of the thus-obtained compound was identified by the $^1$H NMR spectrum of the compound.

$^1$H-NMR (300 MHz, DMSO-d$_6$, δ) 0.88 to 0.92 (m, 6H), 1.33 (br, 12H), 1.81 (br, 4), 2.98 (s, 12H), 3.27 (br, 4H), 4.60 (s, 4H), 7.73 (d, J=8.2 Hz, 4H), 7.94 (d, J=8.9 Hz, 4H), 8.05 (d, J=8.9 Hz, 4H), 8.12 (d, J=8.1 Hz, 4H), 10.68 (s, 2H)

an ambient temperature for 2 hours. Then, the resultant supernatant was collected, to give an SWCNT dispersion containing the single-walled CNT stably.

With the thus-obtained SWCNT dispersion, the visible-near infrared absorption spectrum was measured by using a Vis-NIR spectrophotometer. The result is shown in FIG. 1-*a*. In FIG. 1-*a*, characteristic peaks were observed, which were the same as the peaks in a spectrum of a SWCNT dispersion already reported, and thus it was confirmed, in the above-mentioned SWCNT dispersion, that the bundle of the SWCNT was undone, to be isolatedly dispersed, and that the SWCNT was dissociated in water.

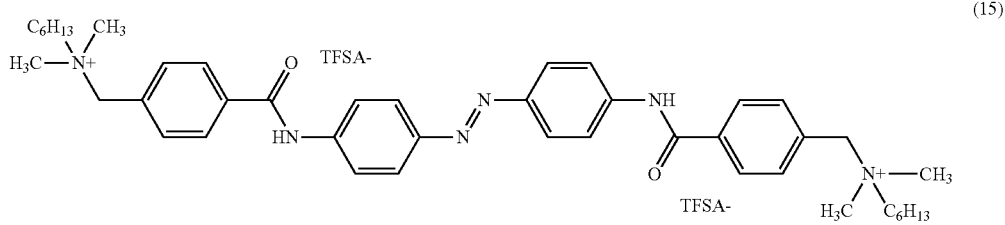

(15)

Example 11

The ionic compound represented by formula (16) was obtained in the same manner as in Example 8, except that the compound of formula (8) was used in place of the ionic compound represented by formula (5) in Example 8. Yield was 100%. The structure of the thus-obtained compound was identified by the $^1$H NMR spectrum of the compound.

$^1$H-NMR (300 MHz, DMSO-d$_6$, δ) 0.97 (t, J=7.2 Hz, 6H), 1.34 (qt, J=7.5 Hz, 4H), 1.81 (br, 4H), 2.99 (s, 12H), 3.27 (br, 4H), 4.60 (s, 4H), 7.74 (d, J=8.3 Hz, 4H), 7.94 (d, J=8.9 Hz, 4H), 8.05 (d, J=9.0 Hz, 4H), 8.12 (d, J=8.3 Hz, 4H), 10.68 (s, 2H)

Figure 2:
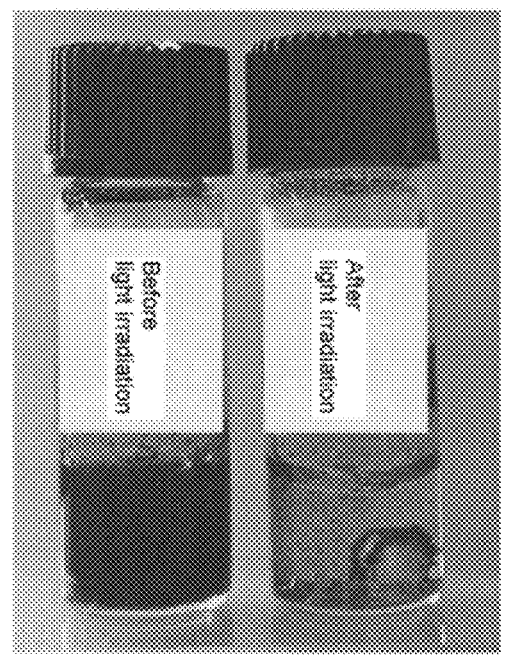
FIG. 2 is a view showing the change in the SWCNT dispersion when the dispersion using the ionic organic compound (12) was irradiated with light in Example 12.

The thus-obtained CNT dispersion (1.5 mL) was collected, transferred to an optical cell of 1-cm square, followed by irradiating with light (3 hours) by using light of 365 nm (LED, intensity 750 mW), under stirring by using a magnetic stirrer, to give a precipitation of the SWCNT, as shown in FIG. 2. The wavelength of the light to be irradiated is not limited to 365 nm, and use may be made of any wavelength of light in the visible to ultraviolet region (from about 200 nm to 600 nm) at which the compound (12) shows absorption.

The change in the solubility was also confirmed by Vis-NIR spectroscopy, in addition to the observation with the naked eye. The result is shown in FIG. 1-*b*. The SWCNT dispersion in which aggregation was occurred by the light

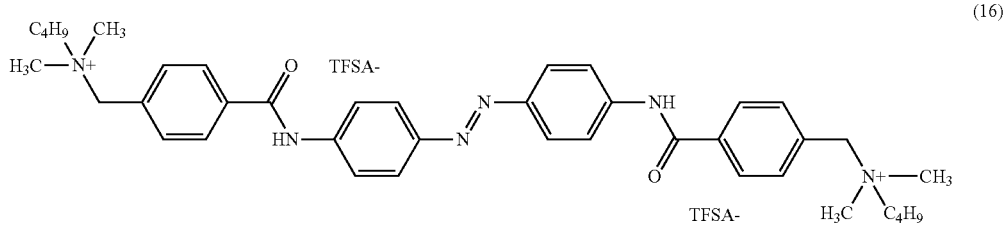

(16)

Example 12

Figure 3:
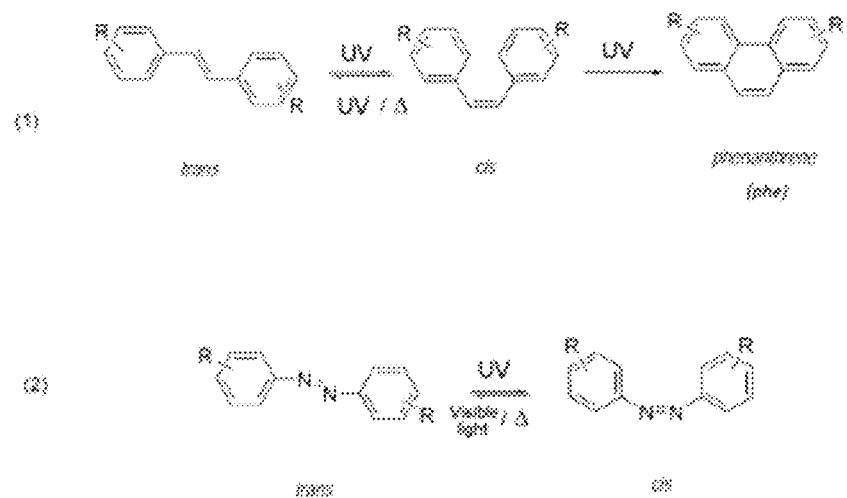
FIG. 3 are diagrams each showing the change in the molecular structure (isomerization) of the dispersant by light stimulation (R is an abbreviation of a side chain moiety).

Preparation of Single-Walled Carbon Nanotube (SWCNT) Dispersion Using Photoresponsive Ion Organic Compound, and Method of Separation by Light Stimulation The ionic organic compound (12) (1.05 mg) obtained in Example 7 was dissolved in 10 mL of deuterium oxide, and 3 mL of the resultant solution was measured off, followed by mixing with 0.98 mg of a single-walled CNT prepared by a High-pressure carbon monoxide (HiPco) method. The thus-mixed liquid was placed in a vial bottle with a size of 13 mL, followed by subjecting to an ultrasonication treatment at 80 W for 30 minutes. Then, the resultant liquid was centrifuged in a centrifugal machine (Hitachi small-size desktop centrifugal machine, CT40), at a rotation speed of 4,000 rpm, under irradiation, was centrifuged, to separate the supernatant, followed by measuring a Vis-NIR spectrum. It was found that the absorbance was decreased drastically, which means occurrence of decrease in the amount of the SWCNT dispersed in the liquid, i.e. aggregation of the SWCNT, by the light irradiation. This is because a photoreaction, i.e. structural change, at the stilbene moiety of the dispersant (12) was induced by the light stimulation, as shown in (1) in FIG. 3, to change the affinity for the carbon nanotube and change the dispersion state of the SWCNT in the liquid.

Similar results were also obtained, by using the ionic organic compounds (4), (5), (10), and (11) obtained in Examples 1, 2, 5, and 6, respectively. Among those, in the cases of (4) and (5), this is because the affinity for the carbon nanotube was changed, by the photoisomerization of the azobenzene moiety of the respective dispersant, as shown in (2) in FIG. 3, to change the dispersion state of the SWCNT in the liquid.

From the above-mentioned results, it was found that the SWCNT in the SWCNT dispersions prepared by using the ionic organic compounds (4), (5), (10), (11), and (12), respectively, can be separated, by irradiating the SWCNT dispersions with light. The concentration range of the ionic organic compound is from about 0.05 g to 20 g/L, preferably from about 0.1 to 5 g/L. Further, the content of the SWCNT dispersible was from 0.1 to 3 g/L.

Example 13

Preparation of Single-Walled Carbon Nanotube (SWCNT) Dispersion Using Photoresponsive Ionic Organic Compound, and Method of Separation by Light Stimulation The photoresponsive ionic organic compound (12) (1.01 mg) obtained in Example 7 was dissolved in 3 mL of deuterium oxide, followed by mixing with 3.6 mg of the single-walled CNT prepared by the High-pressure carbon monoxide (HiPco) method. The thus-mixed liquid was placed in a vial bottle with a size of 13 mL, followed by subjecting to an ultrasonication treatment (80 W, 35 kHz) for 1 hour, by using an ultrasonic washing machine (SHARP UT-105). Then, the resultant liquid was centrifuged (16,400 rpm, 28,500×g) with a cooling centrifugal machine (eppendorf Centrifuge 5417R, FA45-24-11) at room temperature (22° C.) for 3 hours. Then, the resultant supernatant was collected, to give a SWCNT dispersion containing the single-walled CNT stably.

Figure 4:
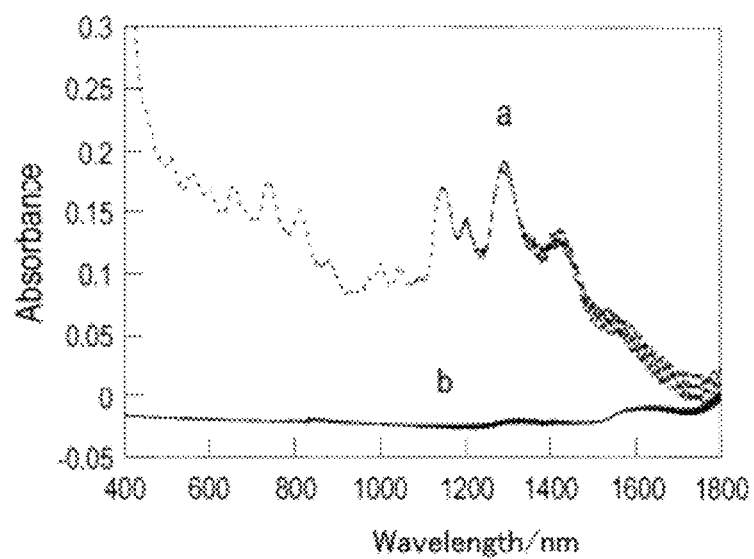
FIG. 4 is a graph showing the Vis-NIR spectrum of the SWCNT dispersion when the ionic organic compound (12) was used in Example 13.

The visible-near infrared absorption spectrum of the thus-obtained SWCNT dispersion was measured by using a Vis-NIR spectrophotometer (SHIMADZU UV-3150). The result is shown in FIG. 4. In FIG. 4a, characteristic peaks were observed, which were the same as the peaks in a spectrum of a SWCNT dispersion already reported, and thus it was confirmed, in the above-mentioned SWCNT dispersion, that the bundle of the SWCNT was undone, to be isolatedly dispersed, and that the SWCNT was dissociated in water.

Figure 5:
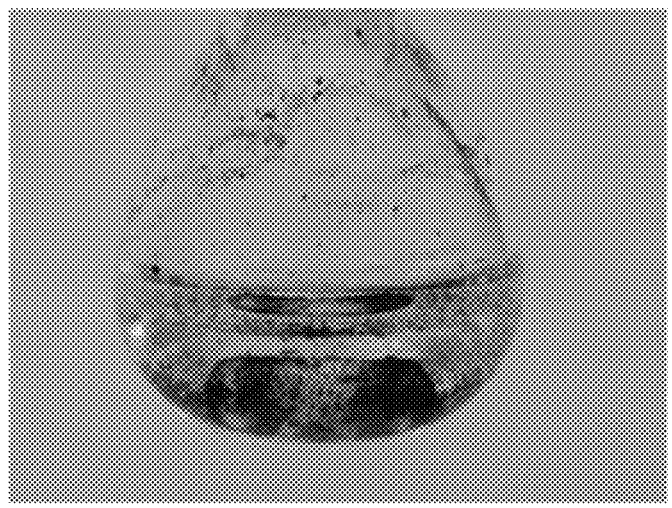
FIG. 5 is a view showing the change in the SWCNT dispersion when the dispersion using the ionic organic compound (12) was irradiated with light in Example 13.

The thus-obtained SWCNT dispersion was transferred to a 10-mL measuring flask, followed by irradiating with light of 365 nm (LED, 750 mW) (15 hours), under stirring by using a magnetic stirrer, to give a precipitation of the SWCNT, as shown in FIG. 5.

The change in the solubility was also confirmed by Vis-NIR spectroscopy, in addition to the observation with the naked eye. The result is shown in FIG. 4b. The SWCNT dispersion in which aggregation was occurred by the light irradiation, was centrifuged with a cooling centrifugal machine (eppendorf Centrifuge 5417R, FA45-24-11) at room temperature (22° C.) (16,400 rpm, 28,500×g, 1 hour), to collect the supernatant, followed by measuring a Vis-NIR spectrum. It was found that the absorbance was decreased drastically, which means occurrence of decrease in the amount of the SWCNT dispersed in the liquid, i.e. aggregation of the SWCNT, by the light irradiation.

Example 14

Figure 6:
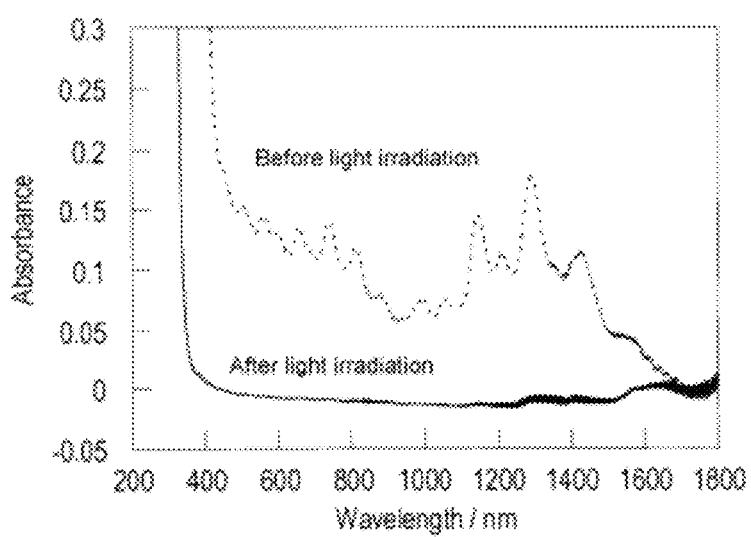
FIG. 6 is a graph showing the Vis-NIR spectra before and after the photoreaction of the SWCNT dispersion when the ionic organic compound (11) was used in Example 14.

Preparation of Single-Walled Carbon Nanotube (SWCNT) Dispersion Using Photoresponsive Ionic Organic Compound, and Method of Separation by Light Stimulation By using the photoresponsive ionic organic compound (11) obtained in Example 6, a dispersion of the single-walled carbon nanotube was prepared in the same manner as in Example 13, to study separation by light stimulation. The change in the NIR spectrum as in FIG. 6 was obtained (before light irradiation: FIG. 6a; after light irradiation: FIG. 6b), and it was found, from the drastic decrease in absorbance, occurrence of decrease in the amount of the SWCNT dispersed in the liquid, i.e. aggregation of the SWCNT, by the light irradiation.

Example 15

Figure 7:
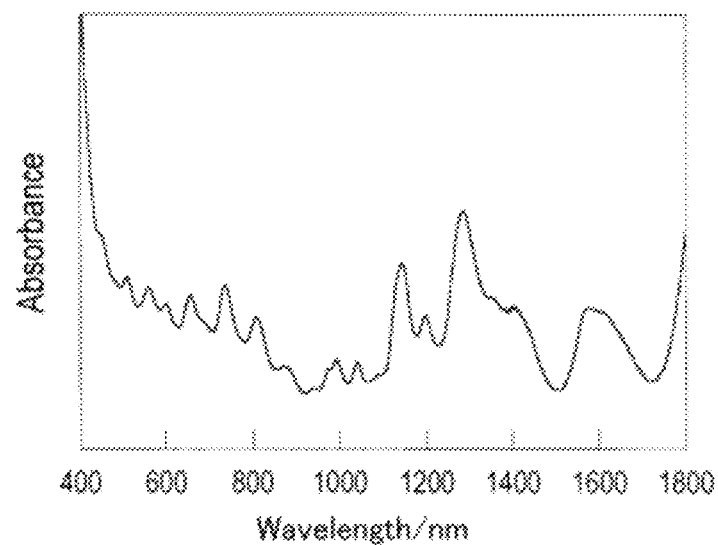
FIG. 7 is a graph showing the Vis-NIR spectrum of the SWCNT dispersion when the ionic organic compound (11) was used in Example 15.
Figure 8:
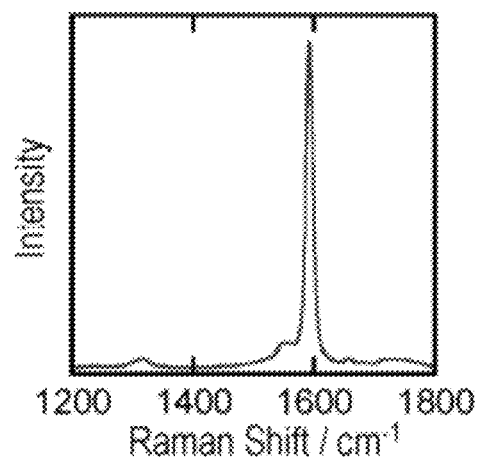
FIG. 8 is a graph showing the Raman spectrum of the SWCNT dispersion when the ionic organic compound (11) was used in Example 15.
Figure 9:
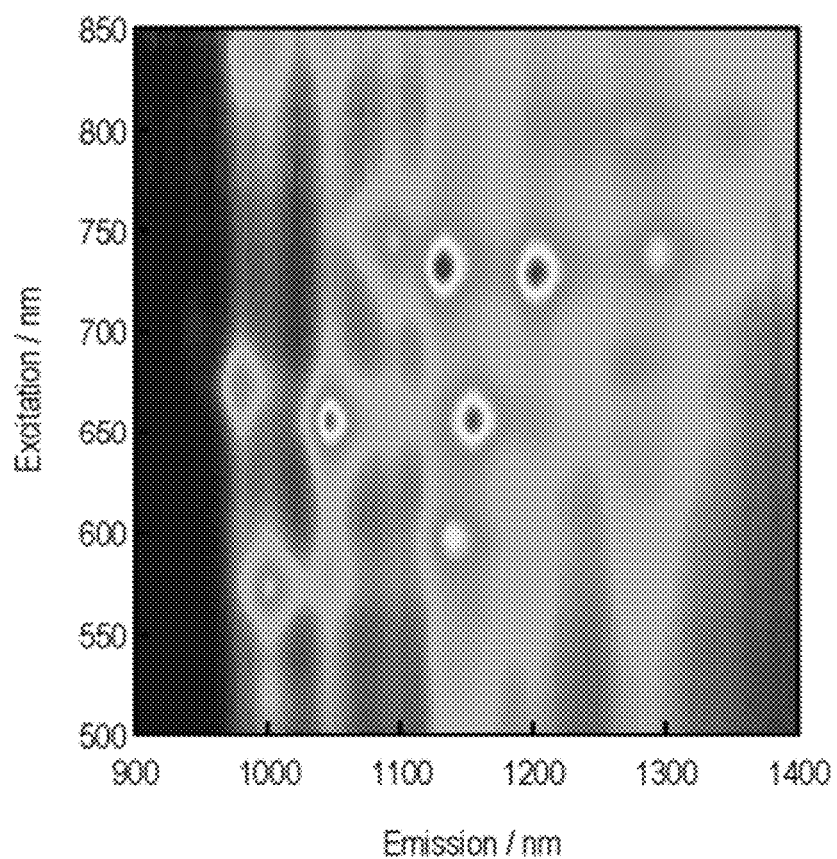
FIG. 9 is a diagram showing the near infrared emission spectrum of the SWCNT dispersion when the ionic organic compound (11) was used in Example 15.

Preparation of Single-Walled Carbon Nanotube (SWCNT) Dispersion Using Photoresponsive Ionic Organic Compound, and Evaluation of Dispersibility The photoresponsive ionic organic compound (11) (10.79 mg) obtained in Example 6 was weighed and dissolved in 20 mL of deuterium oxide, followed by mixing with 6.67 mg of the single-walled CNT prepared by the High-pressure carbon monoxide (Hipco) method. The thus-mixed liquid was placed in a 50-mL wide-mouthed bottle, followed by irradiating with ultrasonic (20 W, 19.9 kHz) for 4 hours by using an ultrasonic homogenizer (BRANSON, Advanced Digital Sonifire 250D), to give a homogeneous dispersion of a black single-walled carbon nanotube. The liquid was placed in a PC pressure-resistant tube (Hitachi Koki, 338455A), followed by ultracentrifuging (58,000 rpm, 216,000×g) for 1 hour by using an ultracentrifugal machine (Hitachi Koki, CS100GXII, a small-size angle rotor S58A), and the resultant supernatant was collected, followed by subjecting to various spectroscopies as mentioned below. An UV-vis-NIR measurement was conducted by using UV3150 manufactured by SHIMADZU (FIG. 7). A Raman spectrum was obtained by measuring backscattered light obtained by exciting (632.82 nm, 1.959 eV) the sample placed in a quartz cell of 1-cm square by a He—Ne laser (NEC GLG5600) by using a monochrometer equipped with a CCD and a notch filter (Bunkokeiki, type M331-1TP). Further, in order to prevent the sample from being warmed by light irradiation, the sample was irradiated with laser beam (10 mW) as a linear beam spot by using a cylindrical lens. The thus-obtained Raman spectrum is shown in FIG. 8. A near infrared emission spectrum was measured by using a fluorescent spectrophotometer (HORIBA, Nanolog) equipped with an InGaAs array detector (cooled by liquid nitrogen). The width of the slit was 7 nm in both excitation and emission. The spectrum was input at 5-nm intervals, and the integration was conducted in 8 seconds. The results are shown in FIG. 9. From those results, characteristic peaks were observed, which were the same as the peaks in a spectrum of a SWCNT dispersion already reported, and thus it was confirmed, in the above-mentioned SWCNT dispersion, that the bundle of the SWCNT was undone, to be isolatedly dispersed, and that the SWCNT was dissociated in water.

Example 16

Figure 10:
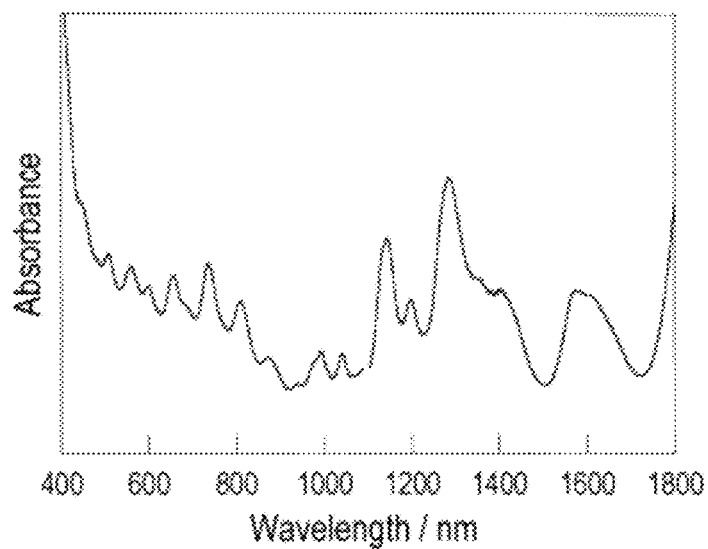
FIG. 10 is a graph showing the Vis-NIR spectrum of the SWCNT dispersion when the ionic organic compound (12) was used in Example 16.
Figure 11:
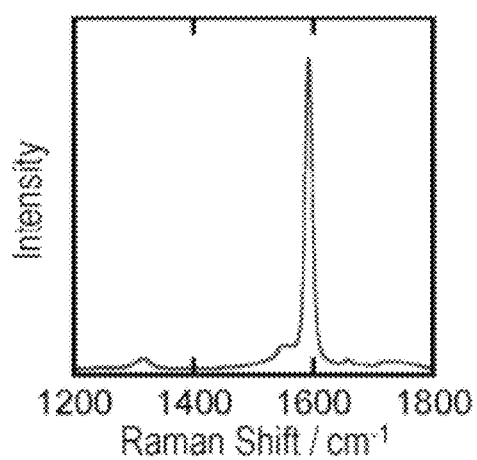
FIG. 11 is a graph showing the Raman spectrum of the SWCNT dispersion when the ionic organic compound (12) was used in Example 16.
Figure 12:
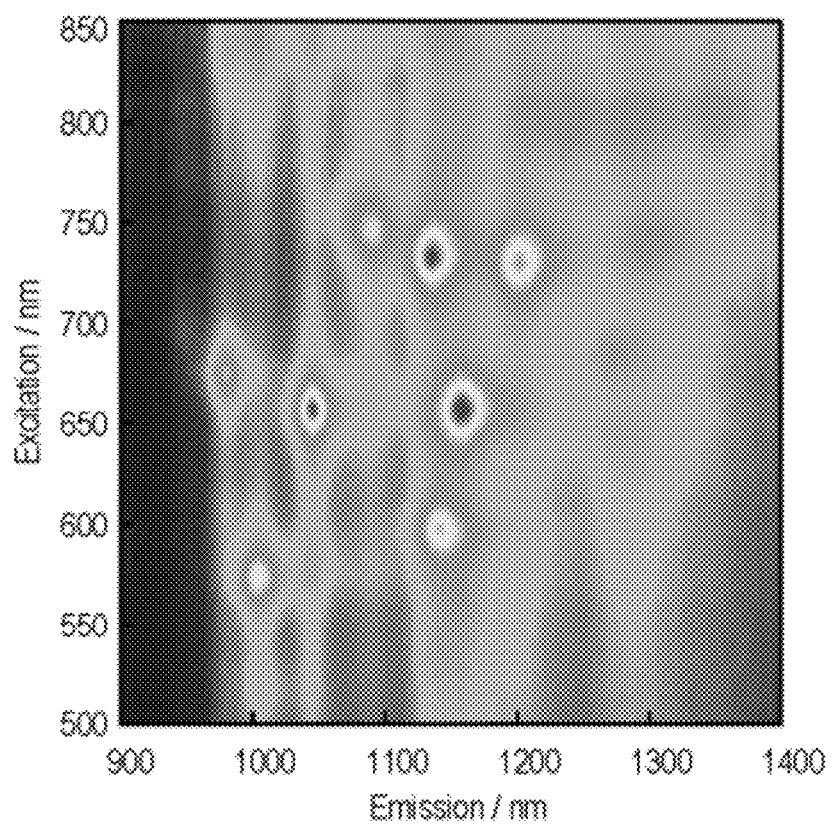
FIG. 12 is a diagram showing the near infrared emission spectrum of the SWCNT dispersion when the ionic organic compound (12) was used in Example 16.

Preparation of Single-Walled Carbon Nanotube (SWCNT) Dispersion Using Photoresponsive Ionic Organic Compound, and Evaluation of Dispersibility With respect to the photoresponsive ionic organic compound (12) obtained in Example 7, the operations were conducted in the same manner as in Example 15, to obtain the results of FIG. 10, FIG. 11, and FIG. 12. From those results, it was confirmed that the bundle of the SWCNT was undone to be isolately dispersed in the SWCNT dispersion, and that the SWCNT was dissociated in water.

Example 17

Figure 13:
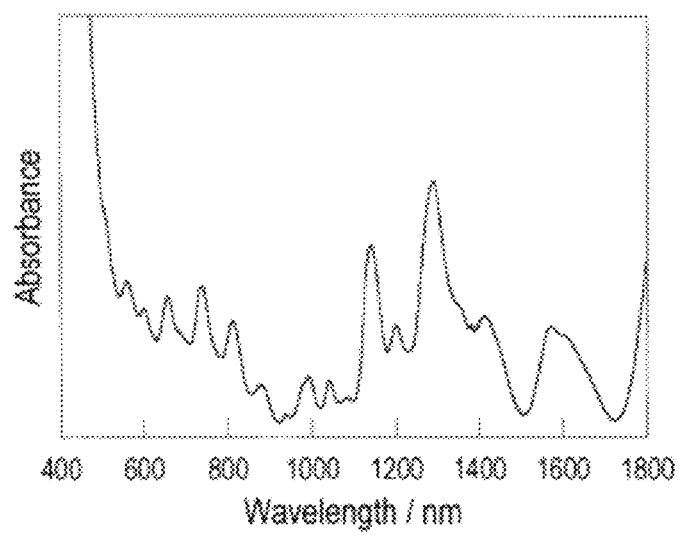
FIG. 13 is a graph showing the Vis-NIR spectrum of the SWCNT dispersion when the ionic organic compound (4) was used in Example 17.
Figure 14:
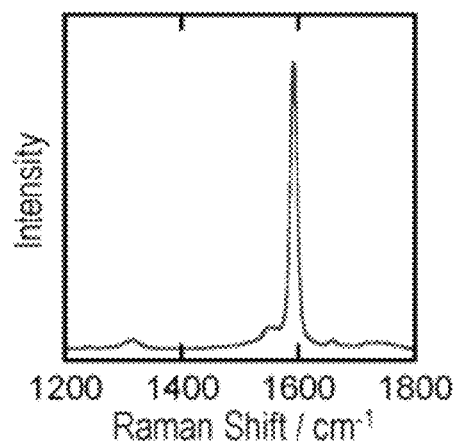
FIG. 14 is a graph showing the Raman spectrum of the SWCNT dispersion when the ionic organic compound (4) was used in Example 17.
Figure 15:
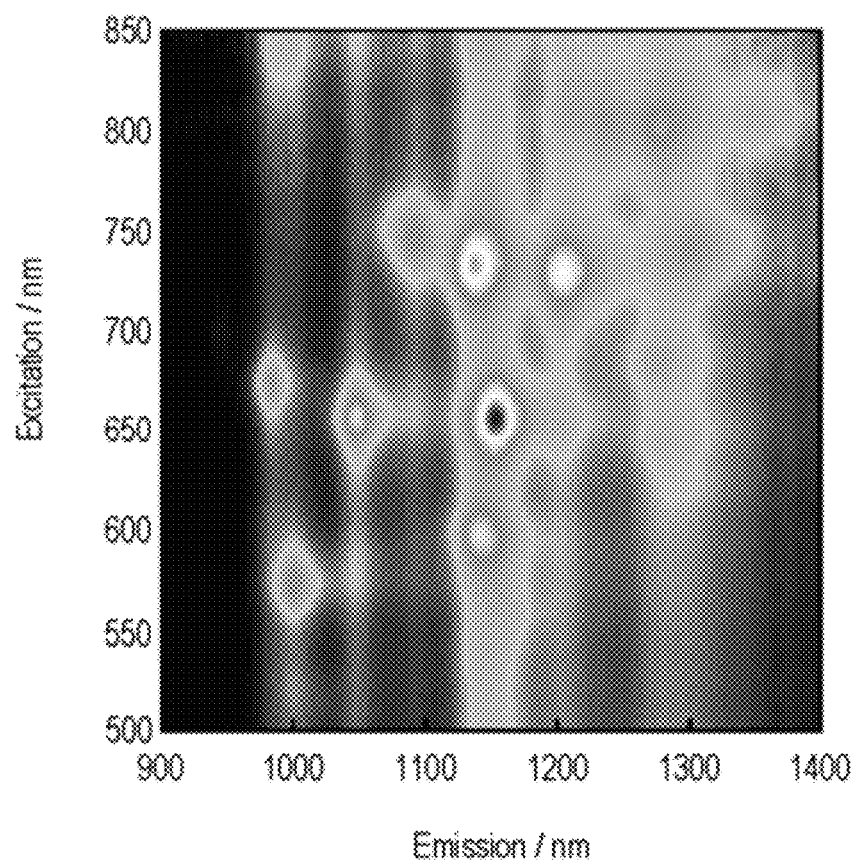
FIG. 15 is a diagram showing the near infrared emission spectrum of the SWCNT dispersion when the ionic organic compound (4) was used in Example 17.

Preparation of Single-Walled Carbon Nanotube (SWCNT) Dispersion Using Photoresponsive Ionic Organic Compound, and Evaluation of Dispersibility With respect to the photoresponsive ionic organic compound (4) obtained in Example 1, the operations were conducted in the same manner as in Example 15, to obtain the results of FIG. 13, FIG. 14, and FIG. 15. From those results, it was confirmed that the bundle of the SWCNT was undone to be isolately dispersed in the SWCNT dispersion, and that the SWCNT was dissociated in water.

Example 18

Analysis of Interaction Between Dispersant and CNT, using PFG-NMR Method

With respect to solutions in which the photoreactive ionic organic compound (11) obtained in Example 6 was dissolved in deuterium oxide at any concentration, and with respect to mixed liquids in which the single-walled CNT prepared by the High-pressure carbon monoxide (Hipco) method was dispersed at any mixing ratio, self-diffusion coefficients were determined by using a pulsed-field gradient NMR (hereinafter PFG-NMR) method to compare the thus-determined coefficients, thereby to study the interaction between the dispersant and the CNT.

The NMR measurement was conducted under the measurement conditions shown below, by using an NMR apparatus (Varian UNITYINOVA 600A (14.1T)) equipped with an H-F{X} diffusion probe (DSI-V218, Doty Scientific). The maximum gradient pulse intensity in the direction Z was about 25 $Tm^{-1}$. Lock and spin were not used. The measurement was conducted at a temperature of 298.15 K (±0.1), and the temperature was calibrated with the chemical shift of methanol. The measurement was conducted, after placing the sample in a 5-mm o.d. Shigemi microcell NMR tube (BMS-005V, Shigemi Co., Ltd.) and adjusting the height of the sample to 5 mm.

The self-diffusion coefficient was evaluated by using a PFG-NMR method (pulsed-field gradient nuclear magnetic resonance method). In PFG-NMR, the diffusion migration distance of a substance, i.e. information on the positions of nuclear spins, can be taken, by applying a pulsed-field gradient (PFG) in the static field direction in a usual NMR measurement. Specifically, it is a method including tracking the attenuation of a subject peak intensity based on the change in PFG intensity, and determining a diffusion coefficient from a gradient by an exponential analysis of the change in the attenuation.

In the actual measurement of a self-diffusion coefficient (D) using PFG-NMR, the evaluation was made by using the Stejskal-Tanner's equation: $\ln(I/I_0) = -D\gamma^2 G^2 \delta^2 (\Delta - \delta/3)$. Specifically, under the assumption that D is in a Gaussian distribution from a negative gradient when a logarithmic signal intensity, when the diffusion time ($\Delta$), length of PFG ($\delta$), and nuclear magnetron ratio ($\gamma$) were fixed and PFG (G) was changed, was plotted against G2, $\ln(I/I_0)$ determined by normalizing the signal intensity I of the dispersant as measured with the signal intensity $I_0$ of water was plotted against $G^2\gamma^2\delta^2(\Delta-\delta/3)$, and a self-diffusion coefficient (D) was determined from the resultant gradient. Further, a PFGSTE method (PFG-stimulated echo method) that is quite effective for a system with a short spin-spin relaxation time period was used in the measurement, and a $[(\pi/2)-\tau_2-(\pi/2)-\tau_1-(\pi/2)-\tau_2-$acquisition] pulse sequence was used.

With respect to the quantification of the freely-diffused dispersant, an extrapolation value in a graph in which $\ln(I/I_0)$ is plotted against $D\gamma^2G^2\delta^2(\Delta-\delta/3)$, i.e. the relative signal intensity ratio $\ln(I/I_0)$, was determined for a single system of the dispersant (before light irradiation and after light irradiation) and a dispersant/CNT mixed system (before light irradiation and after light irradiation), respectively. That is, the relative signal intensity ratio $\ln(I/I_0)$ is free from the attenuation of the peak intensity due to the self-diffusion of the dispersant molecules at G=0, and it is the case where the problem of the affection of the peak of the water existing in a large amount that is observed in a usual $^1$H-NMR spectrum on the quantification of minor components is completely eliminated. Then, utilizing that the I in the thus-determined relative signal intensity ratio reflected the amount of the freely-diffused dispersant, the amount of the freely-diffused dispersant in each condition was calculated.

First, the result obtained for the change in the self-diffusion coefficient in accordance with the photoisomerization reaction of the dispersant alone, is shown in Table 1.

TABLE 1

| Sample | Concentration (M) | Self-diffusion coefficient ($m^2s^{-1}$) |
| --- | --- | --- |
| trans-(11)-1 | $1.43 \times 10^{-3}$ | $7.37 \times 10^{-11}$ |
| trans-(11)-2 | $7.17 \times 10^{-4}$ | $8.60 \times 10^{-11}$ |
| trans-(11)-3 | $3.59 \times 10^{-4}$ | $9.96 \times 10^{-11}$ |
| trans-(11)-4 | $1.79 \times 10^{-4}$ | $9.88 \times 10^{-11}$ |
| phe-(11)-1 | $1.32 \times 10^{-3}$ | $2.02 \times 10^{-10}$ |
| phe-(11)-2 | $6.58 \times 10^{-4}$ | $2.14 \times 10^{-10}$ |
| phe-(11)-3 | $3.29 \times 10^{-4}$ | $2.00 \times 10^{-10}$ |
| phe-(11)-4 | $1.65 \times 10^{-4}$ | $2.06 \times 10^{-10}$ |

From the fact that concentration-dependency was observed little in the self-diffusion coefficients in the dispersant before irradiation of light (trans-(11)) and in the dispersant after irradiation of light (phe-(11)), it was clarified that the dispersant was present as a single molecule, without forming any associated body or the like in the liquid within the studied concentration range. Further, it was confirmed that the self-diffusion coefficient was increased after the photoreaction (phe-(11)), and it was found that the change in the self-diffusion coefficient appeared due to the change in the hydrokinetic radius in accordance with the structural change.

Next, the interaction between the dispersant and the CNT was studied. The self-diffusion coefficients of the dispersant in the mixed liquid of the photoreactive ionic organic compound (11) and the CNT were determined and compared for the case of the dispersant alone, and for before and after the photoreaction. The results are shown in Table 2. In the presence of the CNT, the diffusion coefficient of the dispersant was smaller than that in the state in the solution containing the dispersant alone. This suggested that the diffusion velocity was lowered, since the dispersant and the CNT was caused a chemically-exchanging interaction. Further, when the amount of the freely-diffused dispersant was estimated, it was found that the amount was significantly changed before and after the photoreaction, and that the amount of the freely-diffused dispersant in phe-(11) was increased. This was a result for supporting that the amount of adsorption and adsorbability of phe-(11) on the CNT was lowered.

TABLE 2

| Sample | Concentration of dispersant (M) | Amount of SWCNT (mg) | Self-diffusion coefficient ($m^2s^{-1}$) | Quantified amount of freely-diffused dispersant |
|---|---|---|---|---|
| trans-(11)/CNT | $1.04 \times 10^{-3}$ | 1.08 | $5.54 \times 10^{-11}$ | 0.13 |
| phe-(11)/CNT | $7.75 \times 10^{-4}$ | 1.06 | $1.28 \times 10^{-10}$ | 0.30 |

Example 19

Analysis of Interaction Between Dispersant and CNT, Using PFG-NMR Method

With respect to solutions in which the photoreactive ionic compound (12) obtained in Example 7 was dissolved in deuterium oxide at any concentrations, the self-diffusion coefficients in the dispersant alone and the mixed system with the CNT were determined in the same manner as in Example 18, and the interaction between the photoresponsive ionic compound (12) and the CNT was studied. From the thus-obtained results shown in Table 3 and Table 4, it was found that the change in the self-diffusion coefficient appeared in the compound (12) as in the compound (11), due to the change in the hydrokinetic radius in accordance with the structural change before and after the photoreaction, and it was also found that the amount of the freely-diffused dispersant was changed significantly before and after the photoreaction.

TABLE 3

| Sample | Concentration (M) | Self-diffusion coefficient ($m^2s^{-1}$) |
|---|---|---|
| trans-(12)-1 | $1.81 \times 10^{-3}$ | $9.51 \times 10^{-11}$ |
| trans-(12)-2 | $9.06 \times 10^{-4}$ | $1.05 \times 10^{-10}$ |
| trans-(12)-3 | $4.53 \times 10^{-4}$ | $8.75 \times 10^{-11}$ |
| trans-(12)-4 | $2.26 \times 10^{-4}$ | $9.86 \times 10^{-11}$ |
| phe-(12)-1 | $1.52 \times 10^{-3}$ | $2.55 \times 10^{-10}$ |
| phe-(12)-2 | $7.95 \times 10^{-4}$ | $2.18 \times 10^{-10}$ |
| phe-(12)-3 | $3.80 \times 10^{-4}$ | $2.75 \times 10^{-10}$ |
| phe-(12)-4 | $1.90 \times 10^{-4}$ | — |

TABLE 4

| Sample | Concentration of dispersant (M) | Amount of SWCNT (mg) | Self-diffusion coefficient ($m^2s^{-1}$) | Quantified amount of freely-diffused dispersant |
|---|---|---|---|---|
| trans-(12)/CNT | $9.00 \times 10^{-4}$ | 1.28 | $7.11 \times 10^{-11}$ | 0.11 |
| phe-(12)/CNT | $8.83 \times 10^{-4}$ | 1.23 | $1.59 \times 10^{-10}$ | 0.52 |

The invention claimed is:

1. A photoresponsive ionic organic compound, represented by formula (I):

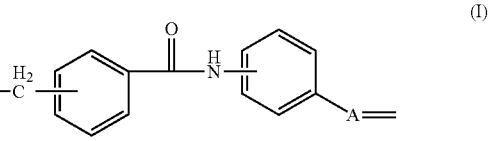
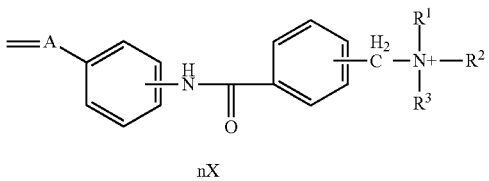

nX wherein $R^1$, $R^2$, and $R^3$ each represent a hydrogen atom or an alkyl group; A represents —CH— or a nitrogen atom; X represents an anion; and n is a number to give a charge of −2 to nX.

2. The photoresponsive ionic organic compound according to claim 1, wherein, in formula (I), X is at least one selected from a halogen atom selected from F, Cl, Br, or I; a tetrafluoroborate group ($BF_4$), hexafluorophosphate ($PF_6$), bis(trifluoromethanesulfonyl)imido (TFSA), thioisocyanate (SCN), a nitrate group ($NO_3$), a sulfate group ($SO_4$), a thiosulfate group ($S_2O_3$), a carbonate group ($CO_3$), a hydrogencarbonate group ($HCO_3$), a phosphate group, a phosphite group, a phosphinate group; a halogen acid compound acid group represented by $AO_4$, $AO_3$, $AO_2$, or AO, in which A represents Cl, Br, or I; a tris(trifluoromethylsulfonyl)carbonate group, a trifluoromethylsulfonate group, a dicyanamido group, an acetate group ($CH_3COO$); a halogenated acetate group represented by $(CA_nH_{3-n})COO$, in which A represents F, Cl, Br, or I, and n is 1, 2, or 3; and a tetraphenylborate group ($BPh_4$) and a derivative thereof represented by $B(Aryl)_4$, in which Aryl represents a substituted phenyl group.

3. A method of producing the photoresponsive ionic organic compound according to claim 1, which method comprises: subjecting (A) a photoresponsive aromatic diamide compound having a (chloromethyl)benzamido group on the respective end, represented by formula (II), and (B) an amine represented by formula (III), to a quaternization reaction:

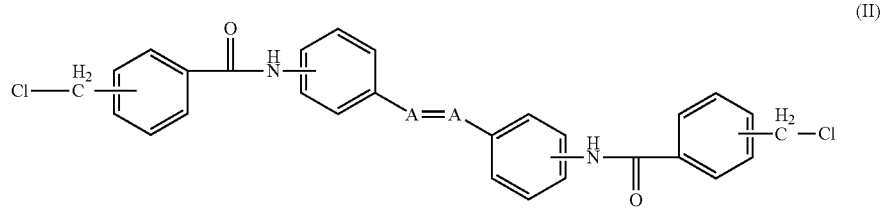

(II)

wherein A represents —CH— or a nitrogen atom; and

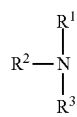

(III)

wherein $R^1$, $R^2$, and $R^3$ each represent a hydrogen atom or an alkyl group.

4. The method of producing the photoresponsive ionic organic compound according to claim 3, which method further comprises: substituting the anion of the thus-obtained photoresponsive ionic organic compound with another anion by an anion exchange reaction.

5. The method of producing the photoresponsive ionic organic compound according to claim 3, wherein the quaternization reaction is conducted in dimethylformamide at from 50 to 80° C.

6. The method of producing the photoresponsive ionic organic compound according to claim 5, which method further comprises: substituting the anion of the thus-obtained photoresponsive ionic organic compound with another anion by an anion exchange reaction.

7. A photoresponsive CNT dispersant, comprising the photoresponsive ionic organic compound according to claim 1.

8. The photoresponsive CNT dispersant according to claim 7, which has a self-diffusion coefficient that changes in response to light.

9. A CNT dispersion, containing the photoresponsive CNT dispersant according to claim 7.

10. The CNT dispersion according to claim 9, wherein the photoresponsive CNT dispersant has a self-diffusion coefficient that changes in response to light.

11. A method of separating a CNT from a CNT dispersion containing the photoresponsive CNT dispersant according to claim 7, which method comprises the steps of:
    irradiating the CNT dispersion with light of a suitable wavelength, to change a molecular structure of the photoresponsive CNT dispersant, thereby to change an affinity thereof with the CNT; and
    controlling a dispersibility of the CNT with the photoresponsive CNT dispersant.

\* \* \* \* \*